Figure 1:
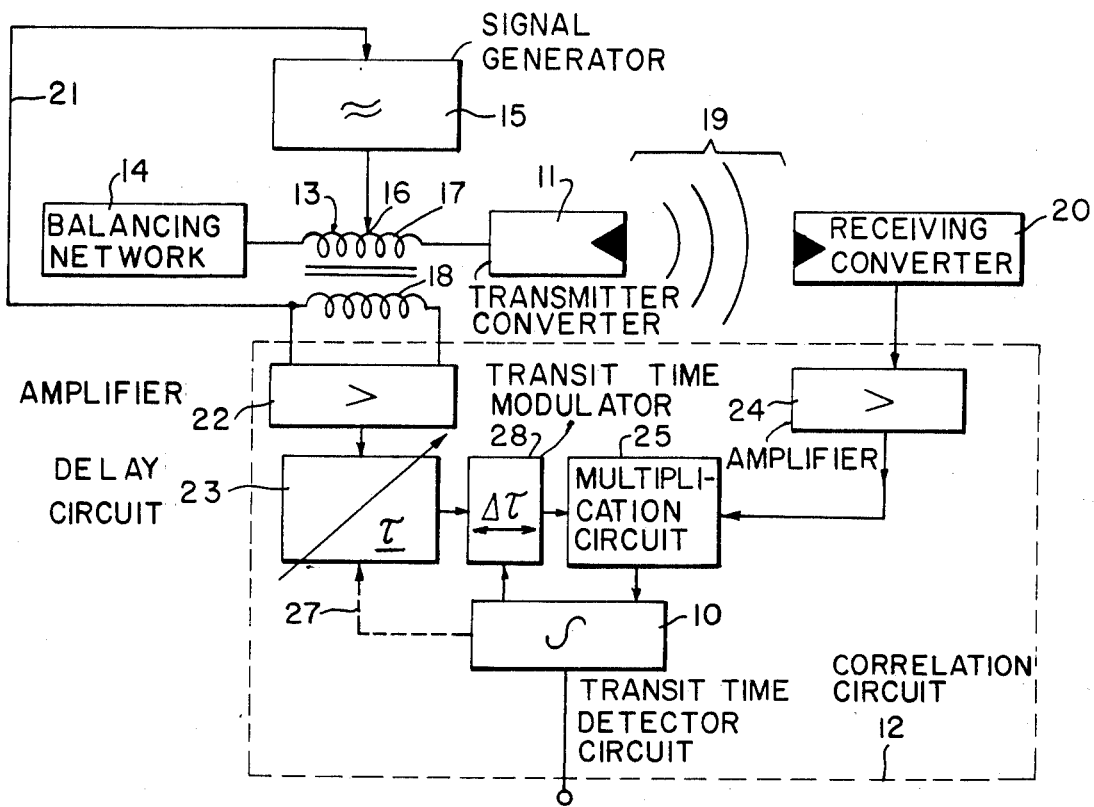

United States Patent [19]

Lauer et al.

[11] Patent Number: 4,576,047

[45] Date of Patent: Mar. 18, 1986

[54] APPARATUS FOR DETERMINING THE TRANSIT TIME OF ULTRASONIC PULSES IN A FLUID

[75] Inventors: Reinhard Lauer, Waldkirch; Werner Hartmann, Emmendingen, both of Fed. Rep. of Germany

[73] Assignee: Erwin Sick GmbH Optik-Elektronik, Waldkirch, Fed. Rep. of Germany

[21] Appl. No.: 606,250

[22] Filed: May 2, 1984

[30] Foreign Application Priority Data

May 6, 1983 [DE] Fed. Rep. of Germany ....... 3316631

[51] Int. Cl.$^4$ .......................... G01F 1/66; G01N 29/02
[52] U.S. Cl. ..................................... 73/597; 73/861.06
[58] Field of Search .......... 73/861.06, 861.27, 861.28, 73/597

[56] References Cited

U.S. PATENT DOCUMENTS 2,826,912  3/1958  Kritz ................................ 73/861.27
3,762,221  10/1973  Coulthard ....................... 73/861.06

Primary Examiner—Herbert Goldstein

[57] ABSTRACT

An apparatus for determining the transit times of ultrasonic pulses in a fluid has at least two electroacoustic converters (11, 20) arranged spaced apart in the fluid. An electrical signal proportional to the sound pressure generated at the transmitting converter (11) is derived from the transmitting converter (11) and is fed to the input of a correlation circuit (12).

4 Claims, 3 Drawing Figures

APPARATUS FOR DETERMINING THE TRANSIT TIME OF ULTRASONIC PULSES IN A FLUID

The invention relates to an apparatus for determining the transit times of ultrasonic pulses in a fluid, in particular in a gas, the apparatus comprising at least two electroacoustic converters arranged spaced apart from each other along a measurement path extending through the fluid of which one transmits ultrasonic pulses along the measurement path while the other receives the pulses which have travelled along the measurement path, and wherein both converters are connected to a correlation circuit in order to determine the transit times of the pulses.

An apparatus of this kind is used in a method of measuring the flow velocity of a gaseous medium. For this purpose ultrasonic pulses are transmitted along a measurement path containing the gaseous medium in a direction such that they have at least component in common with the flow direction of the medium.

In such devices for measuring the speed of flow acoustic pulses are sent along the measuring path located in the flowing gaseous medium at intervals of time and the transit times of the pulses are evaluated. In general ultrasonic pulses are directed in opposite directions along the measurement path and the speed of flow is calculated from the difference between the transit times in two directions. The accurate detection of the transit times (which is for example described in German Offenlegungsschrift No. 30 16 968) is made difficult by short duration disturbances along the transmission path, which distort the acoustic signal, and also by long term changes of the transmitter signal.

In a stochastic method, for example as described in German Offenlegungsschrift No. 31 10 828, in which the cross correlation of two received signals is used which are obtained by scanning two surface areas which are spaced apart from one another, as the disadvantage that the association between the two signals to be compared can be affected, in particular for gas flow measurements, not only by the speed of gas flow but also by other physical parameters, for example differential changes in the transmission behaviour of the two measurement paths.

The principal object underlying the present invention is to use an apparatus of the initially named kind, in particular making use of cross correlation techniques, for signals which are fully correlated with one another in the disturbance free case, namely acoustic transmitted and received signals, with long term changes of the transmitted signal, which could otherwise easily lead to measurement errors, no longer having any disadvantageous effect because the correlation process does not depend on any signal shape.

In order to satisfy this object the invention proposes that an electrical signal proportional to the sound pressure which is generated should be derived from the respective transmitting converter and applied to the input of the correlation circuit. The transmitter signal for the transmitting converter should, in particular, be generated in oscillating operation by means of a hybrid circuit.

An advantageous practical embodiment of the apparatus is constructed in such a way that a signal generator is connected to the central tap of the primary winding of a transformer, with the ends of the primary winding being connected to the transmitting converter and to a balancing circuit which serves to suppress the generator signal in the secondary winding respectively, and that the secondary winding is connected to the correlation circuit. For the purpose of self-excitation of the signal generator the output signal of the transformer should be fed back to the signal generator, in order to allow the signal generator to oscillate at the natural frequency of oscillation of the transmitting converter.

As a result of the construction of the invention the electrical generator signal which excites the ultrasonic transmitting converter is fully suppressed by means of the balancing network so that it does not appear at the output of the transformer. The electrical voltage which corresponds to the membrane deflection of the transmitting converter, and also to the generated pressure signal, is however coupled into the secondary winding of the transformer so that a signal which is directly proportional to the sound pressure signal is present at the output of the transformer. Each change in the behaviour of the transmitter converter will thus have an effect on the signal delivered to the correlation circuit, and can accordingly be taken into account during the correlation with the received signal.

In accordance with the invention piezoelectric composite oscillators are preferably used to convert the acoustic transmitted and received signals into proportional electrical signals. A suitable stochastic transit time measuring process makes it possible to specify the transit time from the maximum of the cross correlation of the transmitted and received signals. The transmitted signal is so generated with the aid of the hybrid network operating as an oscillator that an electrical signal which is proportional to the sound pressure that is generated is coupled into the receiving circuit of the same hybrid network.

As a result of the apparatus of the invention it is possible to use the method of cross correlation for signals which are fully correlated with one another in the disturbance-free case; namely the acoustic transmitted and received signals. Long term changes of the transmitted signal, which could otherwise easily lead to measurement errors are then unimportant because the correlation process does not depend on the signal shape.

Thus, in accordance with the invention, the acoustic signals are converted into a proportional electrical transmitter signal and into a proportional electrical receiver signal.

Figure 2:
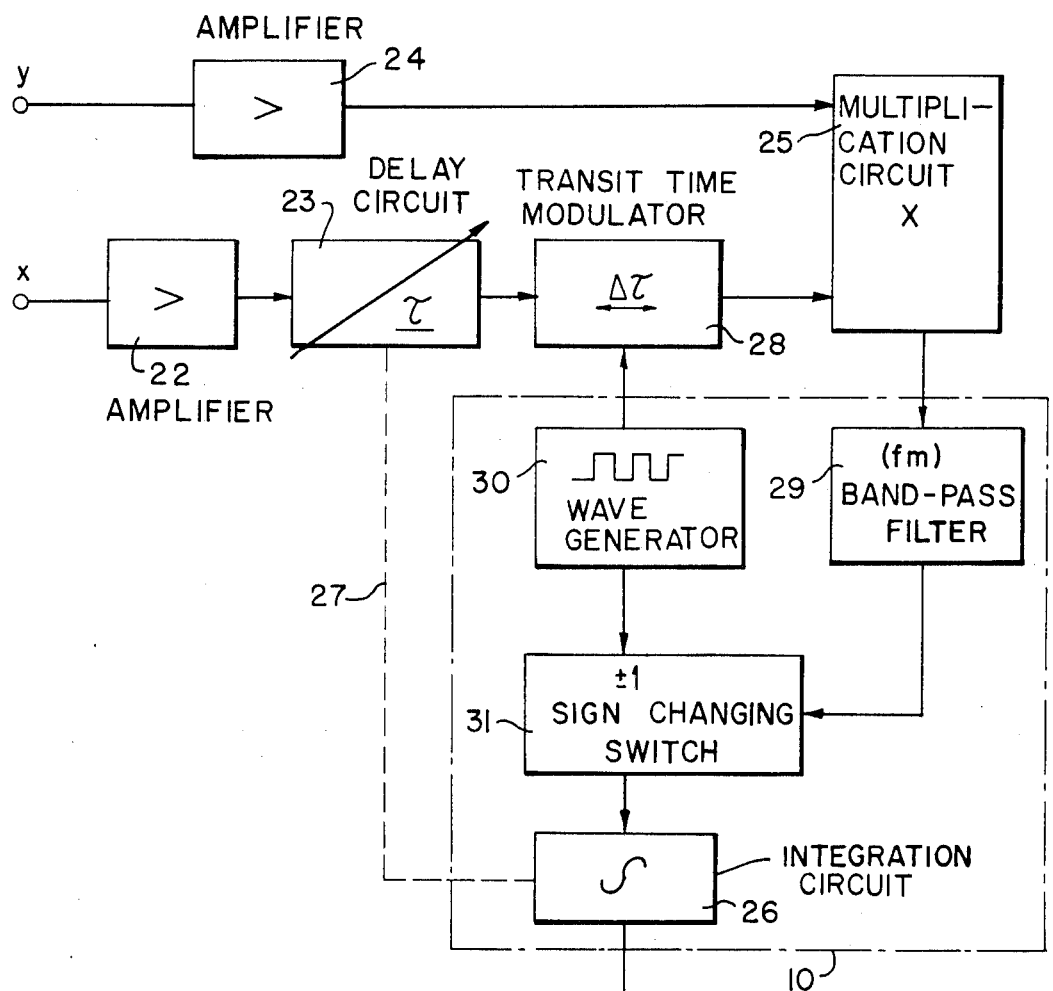
Figure 3:
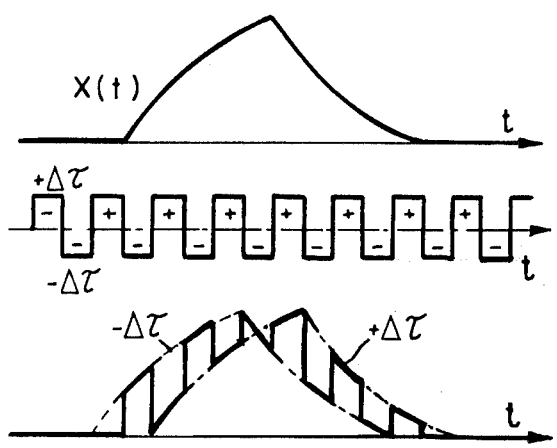

The invention will now be described in the following by way of example and with reference to the drawings which show:

FIG. 1 a simplified block circuit diagram of an apparatus in accordance with the invention for determining the transit time of ultrasonic pulses by cross correlation, FIG. 2 a block circuit diagram of a preferred correlation circuit, and FIG. 3 three signal diagrams which relate to the circuit diagram of FIG. 2 and which have been drawn to the same time scale, with the upper diagram reproducing the delayed transmitter signal, the second diagram representing the transit time modulation, and the third diagram representing the transit time modulated transmitter signal prior to multiplication.

As seen in FIG. 1 an electroacoustic ultrasonic transmitter converter 11 is arranged at one end of a measuring path 19 which extends through a gas in which the transit time of ultrasonic pulses is to be measured. An electroacoustic receiving converter 20 lies opposite to and is spaced from the transmitter converter. Both converters are constructed as composite piezoelectric oscillators. The transmitter converter 11 is fed via the one end of the primary winding 17 of an inductive transformer the other end of which is connected to a balancing network 14. The primary winding 17 also has a central tap 16 to which is applied the output of a signal generator 15 which transmits pulse repetition signals. The balancing network is so constructed, in dependence on the location of the central tap 16, that a magnetic excitation is generated in the half of the primary winding 17 of the transformer 13 associated with the balancing network which opposes the magnetic excitation generated in the other half of the winding by the generator signal, so that in this respect no signal is generated in the secondary winding 18 of the transformer 13.

The secondary winding 18 is however connected to a correlation circuit 12 in the same way as the receiver 20 as will be described in detail later. The output signal of the transformer 13 is moreover fed back to the signal generator 15 via a feedback line 21. In this way a self-excited oscillator circuit is obtained which is automatically tuned to the frequency of the transmitter converter 11. The circuit for generating individual ultrasonic pulses is integrated in the signal generator 15 and is not illustrated in detail.

As a result of the hybrid network 11, 13, 14 of the invention there arises in the secondary winding 18 only an electrical signal which is brought about by the membrane deflection of the transmitter converter 11 and which is proportional to the sound pressure generated by the transmitter converter 11. As a signal proportional to the sound pressure is also transmitted to the correlation circuit 12 from the receiver converter 20 the correlation circuit compares, in the required manner, two signals which are actually fully correlated with one another which leads to an accurate determination of the transit time.

For the sake of simplicity the connection of the individual circuits to earth, particularly in the area of the hybrid network 11, 13, 14 is not shown in detail. The secondary winding 18 of the transformer 13 is connected via an amplifier 22 to a controllable delay circuit 23 by means of which a variable delay $\tau$ can be imposed on the signal coming from the transmitter converter 11 and proportional to the sound pressure signal.

The output of the delay circuit 23 is applied via a transit time modulator 28 to the one input of a multiplication circuit 25. The output signal from the receiver converter 20 is supplied to the other input of the multiplication circuit 25 via an amplifier 24. The output of the multiplication circuit 25 is applied to a transit time detector circuit 10 which makes it possible to form the time average of the product formed in the multiplication circuit 25. The time averaged product at the output of the transit time detector circuit 10 corresponds to the cross-correlation function and can for example be tapped off as a DC voltage the size of which depends on the delay time $\tau$. The time $\tau_0$ which belongs to the maximum of the cross-correlation function is identical with the signal transit time. The DC voltage of the transit time detector circuit 10 can be regulated to this maximum by changing the output delay time $\tau$ in the delay circuit 23. As a signal is passed to the amplifier 22 which is proportional to the ultrasonic pressure generated by the transmitter converter 11 all deformations of the sound pressure signal, caused for example by mechanical shortcomings of the composite piezoelectric oscillator, are taken into account in the correlation circuit 12 of the invention so that these short-comings cannot impair the accuracy of the measurement of the signal transit time $\tau_0$.

The apparatus of the invention can be used anywhere where accurate determination of the transit times of ultrasonic pulses in a fluid is important. The application is thus not restricted to apparatus for the measurement of the speed of a flow of a fluid within the context of which a transit time measurement is necessary.

One construction for the transit time detector circuit 10 can be seen in detail from FIG. 2. As shown in FIG. 2 an integration circuit 26 is present in the transit time detector circuit 10 and the integration time of the integration circuit 26 depends on the rate of measurement, on the carrier frequency of the pulses, on the standard deviation of the transit time, and on the required accuracy of measurement. As a rule of thumb one can assume that the integration time should be larger than or the same as 50 times the duration of one measurement cycle.

The sign of the DC voltage at the output of the transit time detector circuit depends on whether the delay time $\tau$ is smaller or greater than the signal transit time.

A control line 27 can be led back from the output of the transit time detector circuit 10 to the delay circuit 23 in order to automatically regulate this delay circuit so that the output of the transit time detector circuit 10 has a zero passage. The delay time $\tau_0$ which is automatically regulated in this way then corresponds to the signal transit time along the measuring path 19. As previously mentioned FIG. 2 shows a preferred embodiment of the correlation circuit of FIG. 1 and the same reference numerals are used to describe parts common to FIG. 1

The received signal y is again applied to the one input of the multiplication circuit 25 via the amplifier 24. The transmitter signal x, which is proportional to the sound pressure as a result of the hybrid network 11,13,14 of FIG. 1, is again connected to the regulatable delay circuit 23 via the amplifier 22. The transit time modulator 28, by means of which the transmitted pulse signal x with a pulse length approximately 1 ms is, for example, transit time modulated with a frequency of 10 kHz, is again connected between the delay circuit 23 and the multiplication circuit 25. The modulation frequency is delivered from a rectangular wave generator 30 with a frequency of 10 kHz. The modulated transit time has a amplitude $\Delta\tau$ which is the same as the duration of half a period of the modulation frequency.

FIG. 3 shows at the top the ultrasonic transmitter pulse signal x which has been delayed by the delay time $\tau$. Below this there is shown the rectangular modulation signal which originates from the rectangular wave generator 30, and below this again the modulated signal which appears at the output of the transit time modulator 25.

A band-pass filter 29 is connected to the output of the multiplication circuit 25 and is tuned to the frequency of the rectangular wave generator, for example to a frequency of 10 kHz. The band-pass filter 29 thus filters the center frequency of 10 kHz out of the input signal.

Furthermore, a sign changing switch 31 is connected between the band-pass filter 29 and the integration circuit 26. The sign changing switch 31 is connected to the input of the integration circuit 26. In this way an output signal is created at the output of the integration circuit 26 which is equal to zero when the delay time $\tau$ in the delay circuit 23 corresponds to the signal transit time $\tau_0$. If this equalisation has not taken place then the output signal of the integration circuit 26 is either a positive or a negative DC voltage. By feeding this output signal back via the control line 27 the difference between the delay time in the controllable delay circuit 23 and the transit time can be brought to zero in a simple manner.

The delay circuit 23 is preferably constructed as a bucket brigade device.

The advantage of the circuit arrangement described above is the fact that the maximum of the cross-correlation function is present when the transmitted signal is delayed by an amount equal to the transit time. Thus a relatively simple search for the maximum of the cross-correlation function enables the transit time to be determined. This is much simpler and more effective than having to derive the transit time by manipulation of the cross-correlation function.

We claim:

1. Apparatus for determining the transit times of ultrasonic pulses in a fluid, in particular in a gas, the apparatus comprising at least two electroacoustic converters arranged spaced apart from each other along a measurement path extending through the fluid, one converter transmitting ultrasonic pulses along the measurement path while the other converter receives the pulses which have tranvelled along the measurement path, both converters being connected to a correlation circuit having an input, in order to determined the transit times of the pulses, an electrical signal proportional to generated sound pressure being derived from the respective transmitting converter and applied to the input of the correlation circuit.

2. Apparatus in accordance with claim 1, wherein the transmitter signal for the transmitting converter is generated in oscillator operation by means of a circuit comprising a transformer, a transmitting converter connected to the transformer, and a balancing circuit.

3. Apparatus in accordance with claim 2, wherein a signal generator is connected to a central tap of the primary winding of the transformer, with the ends of the primary winding being connected to the transmitting converter and to the balancing circuit for suppressing the generator signal in the secondary winding respectively, the secondary winding being connected to the correlation circuit.

4. Apparatus in accordance with claim 3, wherein the output signal of the transformer is fed back to the signal generator so that the signal generator oscillates at the natural frequency of oscillation of the transmitting converter.

* * * * *